United States Patent [19]

Rokach

[11] Patent Number: 4,535,171

[45] Date of Patent: Aug. 13, 1985

[54] DIBENZO[B,F]THIEPIN-3-CARBOXALDE-HYDES AS PROSTAGLANDIN ANTAGONISTS

[75] Inventor: Joshua Rokach, Laval, Canada

[73] Assignee: Merck Frosst Canada, Inc., Kirkland, Canada

[21] Appl. No.: 540,587

[22] Filed: Oct. 11, 1983

Related U.S. Application Data

[63] Continuation-in-part of Ser. No. 442,921, Nov. 18, 1982, abandoned, which is a continuation of Ser. No. 328,096, Feb. 25, 1981, abandoned, which is a continuation of Ser. No. 097,759, Nov. 27, 1979, abandoned.

[51] Int. Cl.$^3$ ............................................ C07D 337/14
[52] U.S. Cl. ........................................................ 549/12
[58] Field of Search .......................................... 549/12

[56] References Cited

U.S. PATENT DOCUMENTS

| | | | |
|---|---|---|---|
| 3,379,729 | 4/1968 | Protiva | 544/336 |
| 3,509,154 | 4/1970 | Fouche | 544/336 |
| 3,905,989 | 9/1975 | Hodson et al. | 424/269 X |
| 4,025,635 | 5/1977 | Hodson | 424/269 |
| 4,394,515 | 7/1983 | Rokach et al. | |

FOREIGN PATENT DOCUMENTS

| | | | |
|---|---|---|---|
| 0000978 | 3/1979 | European Pat. Off. | 549/12 |
| 0011067 | 5/1980 | Eurpean Pat. Off. | 549/12 |
| 0029587 | 6/1981 | European Pat. Off. | 549/12 |
| 0052912 | 6/1982 | European Pat. Off. | 549/12 |
| 479215 | 4/1979 | Spain. | |
| 479216 | 4/1979 | Spain. | |
| 479217 | 4/1979 | Spain. | |

OTHER PUBLICATIONS

Derwent Abstract 08369Y/05 (1976).
Derwent Abstract 94674x/51 (1976).
Derwent Abstract 56636x/30 (1976).
Chemical Abstracts 73:109723w (1970).
Chemical Abstracts 84:17276b (1976).
Current Abstacts of Chemistry, vol. 66, Issue 718:260474 (1977).
Pelz et al., (Czech.), Collection Chem. Commun. 34 (1969), pp. 3936–3943.
Current Abstracts of Chemistry 69 (1978), No. 269855.

*Primary Examiner*—Ethel G. Love
*Attorney, Agent, or Firm*—Richard A. Elder; Hesna J. Pfeiffer; Julian S. Levitt

[57] ABSTRACT

Novel dibenzo[b,f]thiepin-3-carboxaldehydes and derivatives are prepared and employed in the treatment and control of allergic conditions such as allergic asthma.

12 Claims, No Drawings

DIBENZO[B,F]THIEPIN-3-CARBOXALDEHYDES AS PROSTAGLANDIN ANTAGONISTS

CROSS REFERENCE TO RELATED APPLICATIONS

This application is a continuation-in-part of application Ser. No. 442,921, filed Nov. 18, 1982, now abandoned, which was a continuation of application Ser. No. 328,096, filed Feb. 25, 1981, now abandoned, which was a continuation of application Ser. No. 97,759, filed Nov. 27, 1979, now abandoned.

SUMMARY OF THE INVENTION

This invention relates to prostaglandin antagonists useful in treating a variety of conditions, such as allergic asthma where excessive contractile activity of prostaglandins and prostaglandin biosynthetic intermediate occur. These prostaglandin antagonists are dibenzo[b,f]-thiepin-3-carboxaldehydes or derivatives thereof having the structural formula:

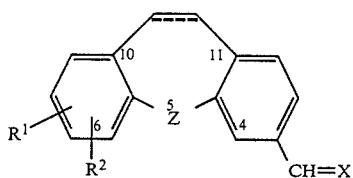

I wherein
Z is sulfinyl, or sulfonyl;
X is O, N—$R^3$, wherein $R^3$ is hydrogen, loweralkyl, aryl, hydroxy, loweralkoxy, loweracyloxy, amino or loweralkylamino; or X may have the formula:

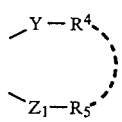

wherein Y and $Z_1$ are each independently $NR_4$, O or S and $R^4$ and $R^5$ are each independently hydrogen or loweralkyl; and the broken line represents a possible bond between $R^4$ and $R^5$ when $R^4$ and $R^5$ are not hydrogen;
$R^1$ and $R^2$ are each independently hydrogen, halogen including chloro, bromo, fluoro and iodo, amino, $C_1$ to $C_4$ alkanoyl, hydroxyl, $C_1$ to $C_4$ alkoxy, thiol, $C_1$ to $C_4$ alkylthio, $C_1$ to $C_4$ alkylsulfinyl, $C_1$ to $C_4$ alkylsulfonyl, trifluoromethyl, trifluoromethylthio, cyano, nitro, and $C_1$ to $C_4$ alkyl or dialkylamino, aralkyl including benzyl and phenethyl, hydroxyalkyl as $CH_3CHOH$; and
the dotted line indicated either an olefinic bond or saturation at the 10-, 11-position.

As used herein, the term halogen (or halo) includes chlorine, bromine, iodine, and fluorine. Unless otherwise specifically stated, the terms loweralkyl and loweralkoxy include straight and branched chain alkyl and alkoxy groups having 1 to 4 carbon atoms in the alkyl or alkoxy moiety such as, for example, methyl, ethyl, n-propyl, isopropyl, n-butyl, methoxy, ethoxy, n-propoxy, and isobutoxy. The term loweralkanoyl includes straight or branched chain alkanoyl groups having 1 to 4 carbon atoms in the alkanoyl moiety such as, for example, formyl, acetyl, propanoyl, and isobutyryl.

The term aralkyl includes straight or branched chain alkyl radicals having one of the hydrogens replaced by a phenyl or substituted phenyl group including phenyl, halophenyl such as chloro, bromo, iodo, and fluorophenyl, nitrophenyl, aminophenyl, hydroxyphenyl, loweralkylphenyl, and the like.

These dibenzo[b,f]thiepin carboxaldehyde derivatives antagonize the actions of contractile prostaglandins, such as $PGF_{2\alpha}$, $PGG_2$, $PGH_2$, and $TXA_2$. The use of agents which act as prostaglandin antagonists offers new approaches to therapy in a number of disease states. For example, certain prostaglandins, such as $PGF_{2\alpha}$, $PGG_2$, and $PGH_2$, are potent contractants of bronchial muscle. Indeed human asthmatics have been shown to be especially sensitive to the bronchial constricting action of $PGF_{2\alpha}$.

In addition to the involvement of contractile prostaglandins in chronic obstructive lung disease (or asthma), prostaglandins are known to play a role in other allergic conditions, as well as inflammation, diarrhea, hypertension, angina, platelet aggregation, cerebral spasm, premature abortion, and dysmenorrhea.

In addition to the prostaglandin antagonist actions, the dibenzo[b,f]thiepins of this invention are antagonists of slow reacting substance of anaphylaxis (SRS-A). This contractile substance is released in the lung tissue in allergic asthma, and antagonism of its actions contributes to alleviation of this disease.

The dibenzo[b,f]thiepins of this invention are prepared according to the following general reaction scheme:

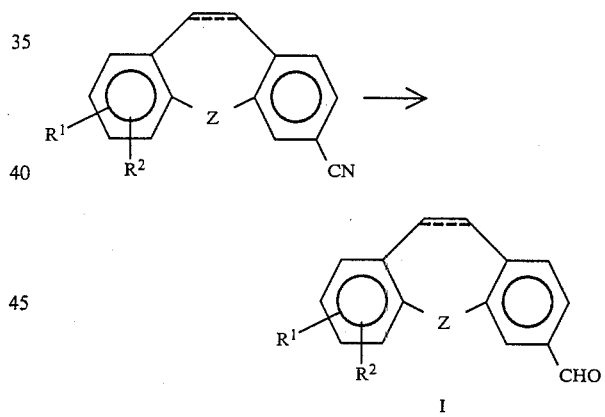

wherein $R^1$, $R^2$, and Z are as defined above.

As shown in the above reaction scheme, an appropriately substituted 3-cyano-dibenzo[b,f]thiepin is reduced and hydrolyzed to the correspondingly substituted dibenzo[b,f]thiepin-3-carboxaldehyde in the presence of a metal containing reducing agent in accordance with the following procedures.

In one method of effecting the conversion of the 3-cyano substituted to a 3-carboxaldehyde substituent, the 3-cyano-dibenzo[b,f]thiepin is treated in dry ether with hydrogen chloride gas and anhydrous stannous chloride at a temperature of 0°–50° C., but preferably between 0°–10° C. Solvents for the reaction are ethers or other inert anhydrous solvents which do not contain an active hydrogen and which will dissolve the reactants. The intermediate which first forms is the imino chloride salt of the amine which is reduced by the action of stannous chloride to the intermediate tin halide complex. This intermediate aldiminium stannic chlorite complex is then hydrolyzed to produce the desired dibenzo[b,f]thiepin-3-carboxaldehyde. In order to isolate the aldehyde from the tin complex, it is sometimes necessary to utilize a chromatographic procedure and/or a second hydrolytic step using an aqueous alcohol solution.

In an alternate procedure for converting 3-cyano-dibenzo[b,f]thiepin-3-carboxaldehydes and the corresponding 10,11-dihydro compounds, the selected cyano compound is treated with from 1–5 parts by weight of Raney alloy (50% Ni/50% Al) in aqueous formic acid. The mixture is stirred at temperatures from 0° C. to reflux temperature, but preferably at the reflux temperature for a period of from 1–24 hours. When the reduction and hydrolysis is complete, the product is recovered by removal of the alloy by filtration while hot, and extraction of the product from the filtrate, followed by crystallization from ethyl acetate.

In a further alternate procedure for the preparation of dibenzo[b,f]thiepin-3-carboxaldehydes or the corresponding 10,11-dihydro derivative, the selected 3-cyano-dibenzo[b,f]thiepin or the 10,11-dihydro derivative employed as starting material is reduced to the corresponding aldehyde by selective reduction with sodium hypophosphite and Raney nickel in aqueous acid (preferably aqueous acetic acid or mixtures containing pyridine in aqueous acetic acid). The reaction is preferably conducted at 25° C., although the temperature may be maintained at from 1°–100° C. to moderate the speed of reaction and/or to increase the yield of product obtained. The product is readily recovered from the reaction mixture after removal of the Raney nickel catalyst by filtration, followed by washing with ethyl acetate to extract any occluded product. The combined filtrate and washings containing the product are then extracted with a mixture of ethyl acetate and ether and the product obtained as a solid residue by evaporation of the solvents from product-containing extract.

In a further alternate procedure for preparing dibenzo[b,f]thiepin-3-carboxaldehydes, the corresponding 10,11-dihydro-3-hydroxymethyldibenzo[b,f]thiepin, or a 10,11-dihydro compound is oxidized by means of pyridinium chlorochromate in an inert solvent such as dichloromethane, at a temperature between 0° C. and reflux temperature, but preferably at room temperature, for a period of 1–24 hours. When oxidation is complete, the mixture is filtered through a bed af Florisil and then washed through with the solvent. Evaporation of the filtrate affords the dibenzo[b,f]thiepin-3-carboxaldehyde which may be purified by chromatography and/or recrystallization as may be appropriate.

A further alternate procedure is employed when the starting material contains a reducible substituent such as a nitro group. In such instances, the substituted e.g., 8-nitro-dibenzo[b,f]thiepin-3-carboxylic acid chloride is reduced with lithium tri-tert-butoxy-aluminum hydride in tetrahydrofuran at −78° C.

Products which may be obtained directly by reduction of the appropriate nitrile are dibenzo[b,f]thiepin-3-carboxaldehyde and dibenzo[b,f]thiepin-3-carboxaldehyde-5,5-dioxide or derivatives bearing $R_1$ and $R_2$ substituents which are resistant to the reducing effect of the reaction conditions employed. Ordinarily the dibenzo[b,f]thiepin-5-oxide or $R_1$, $R_2$ derivatives thereof are prepared by oxidation of the corresponding dibenze[b,f]thiepin with organic peroxides such as peroxy acids like m-chloroperbenzoic acid. The oxidation can be carried further, if an additional equivalent of acid is employed, to produce the corresponding dibenzo[b,f]thiepin-5,5-dioxides. It will be apparent to one skilled in the art that variations in these preparative schemes will allow one to prepare a variety of substituted dibenzo[b,f]thiepin-3-carboxaldehydes, as well as the corresponding thiepin-5-oxides and the thiepin-5,5-dioxides.

From the above-described aldehydes, other compounds of Formula I can be readily prepared by well-known methodology. These include, inter alia, oximes, o-acetyloximes, o-alkyloximes, hydrazones, Schiff bases, acetals, thioacetals and the like.

PREPARATION OF STARTING MATERIALS

As described in greater detail in European Patent Application No. 11,067, an appropriately substituted mercaptobenzoic acid II is reacted with m-dibromobenzene III ($R_3$=Br) to obtain the o-(3-bromophenylthio)-benzoic acid IV. Or alternatively, an appropriately substituted o-bromobenzoic acid II ($R_2$=Br) is reacted with m-bromobenzethiol III ($R_3$=SH) to give IV:

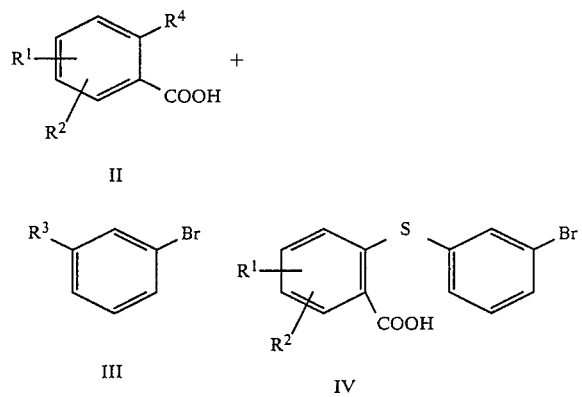

where $R_1$ and $R_2$ are each selected from hydrogen, nitro, amino, $C_1$ to $C_4$ alkanoyl, hydroxyl, $C_1$ to $C_4$ alkoxy, $C_1$ to $C_4$ alkylsulfinyl, $C_1$ to $C_4$ alkylsulfonyl, and $C_1$ to $C_4$ alkyl, trifluoromethyl, and trifluoromethylthio. $R_2$ and $R_3$ are different and alternatively are thiol and bromo.

Generally, the sulfide-forming reaction is carried out according to the methods described by Jilek et al., Monatsh. Chem. 96, 200 (1965); Protiva et al., Czechoslovakian Patent 121,337, Chem. Abstracts 68: 105,247t (1968); and U.S. Pat. No. 3,711,489; and by other procedures well known in the art.

The resulting o-(3-bromophenylthio)benzoic acid (IV) is reduced to the alcohol, brominated, and the bromo replaced with cyano. The cyano derivative is then hydrolyzed to the carboxylic acid V.

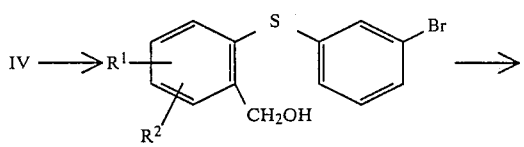

-continued

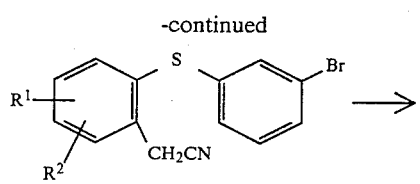

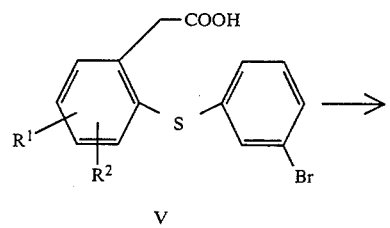

V

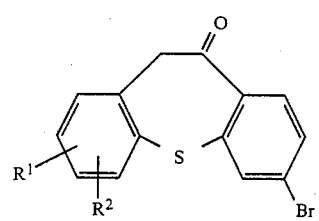

VI

The carboxylic acid V is transformed into the 3-bromo-11-oxo-10,11-dihydrodibenzo[b,f]thiepin by first conversion to the acid halide with thionyl or phosphoryl halide followed by Friedel-Crafts cyclization with a Lewis acid such as aluminum chloride to give VI. Reduction of the ketone VI with alkali metal borohydrides, followed by heating with catalytic amounts of a mineral acid, such as sulfuric acid or toluenesulfonic acid provides the 3-bromodibenzo-[b,f]thiepin VII.

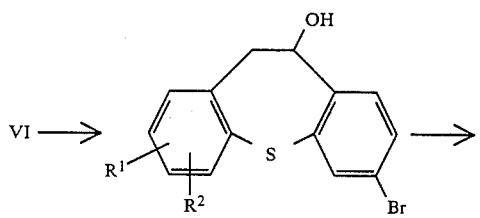

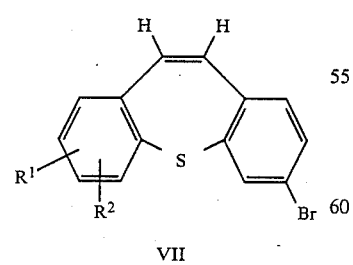

VII

The 3-bromo derivatives VII is then converted to the 3-nitrile VIII by reaction with cuprous cyanide in a high boiling polar solvent such as dimethylformamide, N-methylpyrrolidone, and the like.

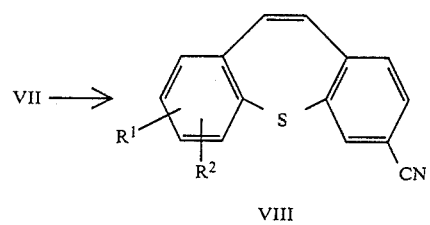

VIII

The cyano intermediate VIII may be oxidized with organic peroxides such as peroxy acids, for example, m-chloroperbenzoic acid and the like, in a stepwise fashion to the corresponding sulfoxide XI and sulfone XII, controlling the molar ratio of oxidant to reductant. This determines the oxidation level of the sulfur. For example, a 1:1 molar ratio results largely in the production of sulfoxide XI. In contrast, a 2:3 molar excess of oxidant results in a yield predominantly comprising the sulfone XII.

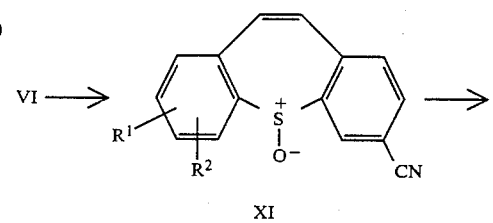

XI

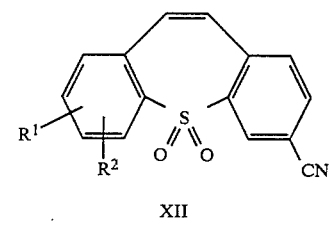

XII

Compounds of type I where the 10,11 double bond is saturated are prepared from intermediate V in which the 3-bromo is converted to a cyano derivative XVII.

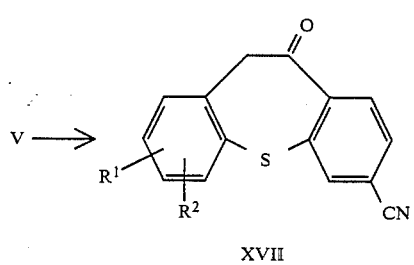

XVII

The compound XVII is reduced by conventional methods, e.g., Wolff-Kishner, to compound XXII.

XVII ⟶ 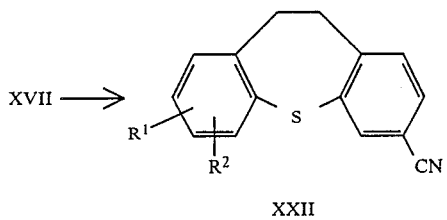

XXII

Substituent R in I can also be introduced by modification of the nitro group in VIII (R=NO₂) by known procedures. For example, XXXIII can be reduced with stannous chloride in acidic medium, hydrochloric acid, and the like, to yield XXXIV which can be hydrolyzed with mineral acids or bases to XXXV.

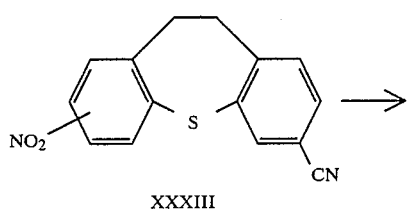

XXXIII

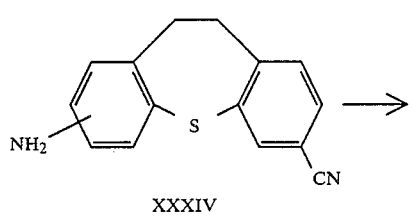

XXXIV

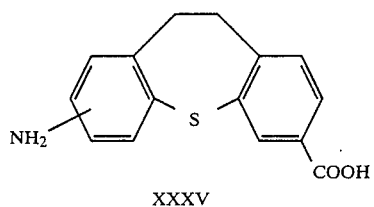

XXXV

Alternatively, XXXIII may be oxidized with peroxides, for example, m-chloroperbenzoic acid to yield XXXVI which can be reduced to XXXVII and then hydrolyzed with mineral acids or bases to XXXVIII.

XXXIII ⟶ 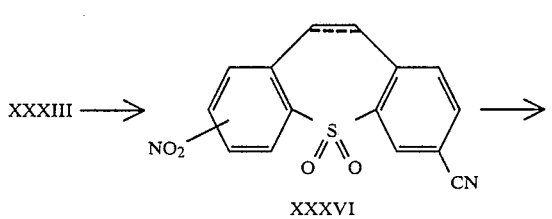

XXXVI

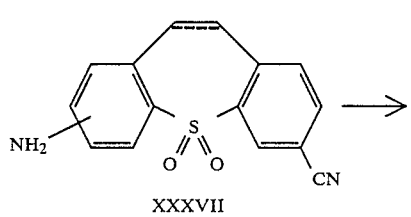

XXXVII

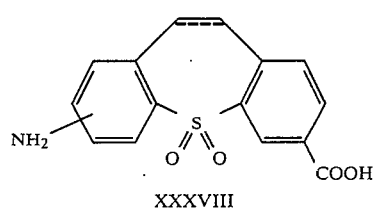

XXXVIII

Intermediate XXXIV can be reacted with sodium nitrite in mineral acid to the diazonium salt XXXIX, where X is a mineral acid counter ion, for example, Cl⁻, HSO₄⁻, BF₄⁻, and the like, which on reaction with CuCl and CuCl₂ yields intermediate XL which can be hydrolyzed to the acid XLI. Intermediate XL may also be oxidized to the sulfone derivative.

XXXIV ⟶ 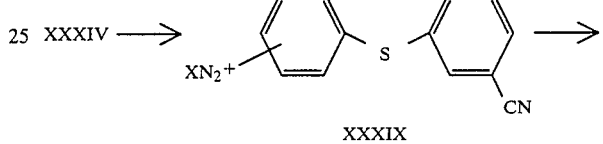

XXXIX

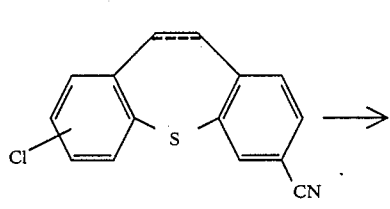

XL

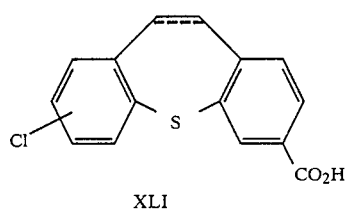

XLI

Compound XXXVII can be transformed in the usual manner to the diazonium salt XLV.

XXXVII ⟶ 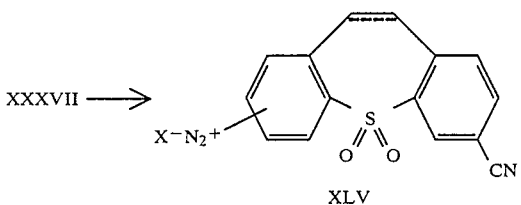

XLV

The 3-hydroxymethyldibenzo[b,f]thiepin and the 10,11-dihydro compounds which may be used as intermediates for the preparation of the title compounds may be made by reduction of the corresponding dibenzo[b,f]thiepin-3-carboxylic acids or esters as described in detail in European Patent Application No. 11,067.

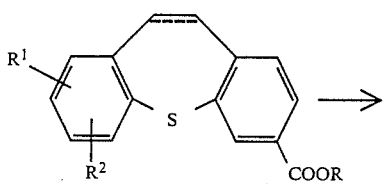

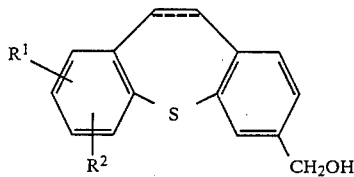

These alcohols may be oxidized to the sulfinyl or sulfonyl oxidation levels by a peroxy acid, for example m-chloroperbenzoic acid or the like, in a stepwise fashion as described for the nitriles VI and XI above.

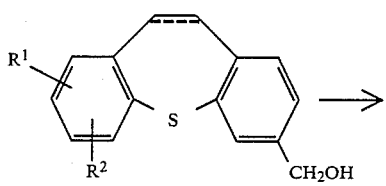

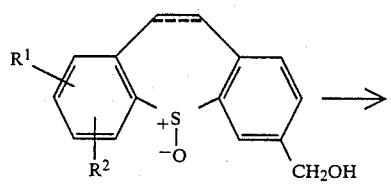

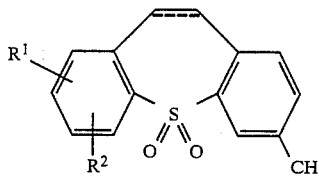

EXAMPLE 1

Dibenzo[b,f]thiepin-3-carboxaldehyde 5,5-dioxide

Mix 267 mg (1 mmole) 3-cyano-dibenzo[b,f]thiepin-5,5-dioxide with Raney allowy (500 mg) and a mixture of 4 ml formic acid and 1 ml water at the reflux temperature. After 3 hours, add 200 mg additional Raney alloy and heat for one hour to obtain complete reduction. Filter the reaction mixture while hot to remove the alloy, and wash with ethyl acetate to remove any occluded solvent. Wash the organic layer containing the product with water and with saturated sodium chloride solution. Separate the organic layer containing the product to produce a residue of a pale yellow oil, which crystallizes in a small volume of ethyl acetate, m.p. 167°–171° C.

EXAMPLE 2

Dibenzo[b,f]thiepin-3-carboxaldehyde-5,5-dioxide

Mix 267 mg (1 mmole) of 3-cyano-dibenzo[b,f]thiepin-5,5-dioxide, 10 ml pyridine, 5 ml acetic acid, and 5 ml water. Add 0.5 g sodium hypophosphite and approximately 0.1 g Raney nickel. Stir at 25° C. for 24 hours and then at 45°–50° C. for 2 hours. Filter the reaction mixture to remove the catalyst and wash any product from the catalyst using 10 ml ethyl acetate. Add 10 ml 6N hydrochloric acid and separate the organic layer containing the product. Evaporate the organic layer to obtain a solid residue comprising the title product, m.p., 175°–177° C. Swishing with methanol and drying the residue gives product melting at 177°–178° C.

EXAMPLE 3

Dibenzo[b,f]thiepin-3-carboxaldehyde

Saturate a suspension of anhydrous stannous chloride (378 mg; 2 mmole) in 7.5 ml dry ether with hydrogen chloride at a temperature of 0°–5° C., and add 235 mg (1 mmole) of 3-cyano-dibenzo[b,f]thiepin. Stir for one hour at 0° C. and allow to warm to room temperature (25° C.). Continue stirring at room temperature for approximately 48 hours. Add 5 ml of water and 1 ml 2N hydrochloric acid, and extract with a mixture of 5 ml ether and 5 ml ethyl acetate. When the hydrolysis of the chloro stannate is complete, evidenced by the disappearance of solids from the solution, separate the organic layer containing the product, wash with water/sodium chloride solution, and after drying, evaporate the solution to produce a dark oil which solidifies when triturated with hexane. The title product is obtained when the above solid material is crystallized from acetonitrile, m.p. 114.5°–115.5° C.

EXAMPLE 4

Dibenzo[b,f]thiepin-3-carboxaldehyde-5-oxide

Dissolve 512 mg (2 mmole) of 3-hydroxymethyl-dibenzo[b,f]thiepin 5-oxide in 50 ml of methylene chloride and add 648 mg (3 mmole) of pyridinium chlorochromate. Stir at room temperature for 1.5 hours and then filter the mix through a bed of Florisil. Wash the Florisil with dichloromethane; and to the combined filtrate add 4 g of silica gel. Evaporate the suspension to dryness, and place the solid on top of a column of 50 g of silica and elute the title compound with a 1:9 mixture of ethyl acetate and toluene. The compound has a m.p. of 188°–190° C.

EXAMPLE 5

10,11-Dihydro-dibenzo[b,f]thiepin-3-carboxaldehyde

Mix 4.74 g (20 mmole) of 3-cyano-10,11-dihydro-dibenzo[b,f]thiepin with 7.56 g (40 mmole) anhydrous stannous chloride and 150 ml ether saturated with anhydrous hydrogen chloride. Stir the mixture at 25° C. for approximately 50 hours to produce a crystalline solid suspended in the reaction mixture. Shake the crystalline solid with 200 ml ice water, and extract with 150 ml ethyl acetate using methanol to dissolve any residual lumpy yellow solid. Separate the ethyl acetate layer containing the product, and after washing with water/saturated chloride solution and drying, the ethyl acetate is removed by evaporation to produce as a residue an amber-colored oil, which crystallizes overnight. Distill the crystalline residue under reduced pressure at 145° C. at 0.04 mm. The distilled product crystallizes, m.p. 55.5°–56.5° C.

EXAMPLE 6

10,11-Dihydro-dibenzo[b,f]thiepin-3-carboxaldehyde-5-oxide

Mix 2.84 g (11.83 mmole) of 10,11-dihydrodibenzo[b,f]thiepin-3-carboxaldehyde with 90 ml methylene chloride at 0° C. Add 2.3 g (11.33 mmoles) of 85% m-chloroperbenzoic acid, followed by the addition of 100 ml methylene chloride. Stir for 2 hours, and then add 4.6 g calcium hydroxide to the resulting clear solution at room temperature. After stirring the suspension for 15 minutes, filter to remove the inorganic solid, and evaporate the filtrate containing the dissolved product to dryness, producing as a residue a dry solid comprising the title product. Purify by recrystallization from acetonitrile, m.p. 158.5°–160° C.

EXAMPLE 7

10,11-Dihydro-dibenzo[b,f]thiepin-3-carboxaldehyde-5,5-dioxide

Repeat the procedure of Example 4, substituting an equivalent amount of 10,11-dihydro-3-hydroxymethyldibenzo[b,f]thiepin-5,5-dioxide in place of 3-hydroxymethyldibenzo[b,f]thiepin-5-oxide to obtain the title compound, m.p., 135°–136° C.

EXAMPLE 8

8-Fluoro-dibenzo[b,f]thiepin-3-carboxaldehyde

Dissolve 568 mg (2.2 mmole) of 2-fluoro-7-hydroxymethyldibenzo[b,f]thiepin in 30 ml of methylene chloride and add 647 mg of 98% pyridinium chlorochromate. Stir the mixture and follow the reaction by thin layer chromatography (Merck silica gel F254 with 5% ethyl acetate in toluene). When complete, filter the mixture through a bed of Florisil, and wash through with methylene chloride. Evaporate the filtrate to obtain a brown solid (600 mg). Purify the crude product by chromatography on silica gel using totluene as solvent to obtain the title compound as a yellow solid, m.p. 137°–139° C.

EXAMPLE 9

8-Fluoro-dibenzo[b,f]thiepin-3-carboxaldehyde-5-oxide

Repeat the procedure of Example 4, substituting an equivalent amount of 3-hydroxymethyl-8-fluorodibenzo[b,f]thiepin-5-oxide in place of the 3-hydroxymethyldibenzo[b,f]thiepin-5-oxide to obtain the title compound, m.p., 212°–214° C.

EXAMPLE 10

8-Fluoro-dibenzo[b,f]thiepin-3-carboxaldehyde-5,5-dioxide

Repeat the procedure of Example 4, substituting an equivalent amount of 3-hydroxymethyl-8-fluorodibenzo[b,f]thiepin-5,5-dioxide in place of 3-hydroxymethyldibenzo[b,f]thiepin-5-oxide to obtain the title compound, m.p., 200°–202° C.

EXAMPLE 11

8-Fluoro-10,11-dihydrodibenzo[b,f]thiepin-3-carboxaldehyde

Proceeding as in Example 4, but starting with 0.5 g (1.9 mmole) of 8-fluoro-3-hydroxymethyl-10,11-dihydrodibenzo[b,f]thiepin, there is obtained 0.42 Ag (84%) of 8-fluoro-3-formyl-10,11-dihydrodibenzo[b,f]thiepin, m.p., 78°–79° C.

EXAMPLE 12

8-Fluoro-10,11-dihydrodibenzo[b,f]thiepin-3-carboxaldehyde-5-oxide

Proceeding as in Example 4, but starting with 0.5 g (1.8 mmole) of 8-fluoro-3-hydroxymethyl-10,11-dihydrodibenzo[b,f]thiepin-5-oxide, there is obtained 0.38 g (77%) of 8-fluoro-3-formyl-10,11-dihydrodibenzo[b,f]thiepin-5-oxide, m.p., 188°–189° C.

EXAMPLE 13

8-Fluoro-10,11-dihydrodibenzo[b,f]thiepin-3-carboxaldehyde-5,5-dioxide

Proceeding as in Example 4, but starting with 0.5 g (1.7 mmole) of 8-fluoro-3-hydroxymethyl-10,11-dihydrodibenzo[b,f]thiepin-5,5-dioxide, there is obtained 0.43 g (87%) of 8-fluoro-3-formyl-10,11-dihydrodibenzo[b,f]thiepin-5,5-dioxide, m.p., 155°–156° C.

EXAMPLE 14

8-Aminodibenzo[b,f]thiepin-3-carboxaldehyde-5,5-dioxide

Repeat the procedure of Example 2, substituting an equivalent quantity of 8-amino-3-cyanodibenzo[b,f]thiepin-5,5-dioxide in place of 3-cyanodibenzo[b,f]thiepin-5,5-dioxide to obtain the title product.

EXAMPLE 15

8-Chlorodibenzo[b,f]thiepin-3-carboxaldehyde

Repeat the procedure of Example 3, substituting an equivalent quantity of 8-chloro-3-cyano-dibenzo[b,f]thiepin for the 3-cyanodibenzo[b,f]thiepin to obtain the title product.

EXAMPLE 16

8-Chlorodibenzo[b,f]thiepin-3-carboxaldehyde-5-oxide and 5,5-dioxide

Repeat the procedure of Example 6, substituting an equivalent quantity of 8-chlorodibenzo[b,f]thiepin-3-carboxaldehyde in place of the 10,11-dihydrodibenzo[b,f]thiepin-3-carboxaldehyde to obtain the title 5-oxide compound.

Repeat the above procedure using twice the equivalent amount of m-chloroperbenzoic acid to obtain the corresponding 5,5-dioxide.

EXAMPLE 17

8-Hydroxydibenzo[b,f]thiepin-3-carboxaldehyde

Repeat the procedure of Example 2, substituting an equivalent quantity of 3-cyano-8-hydroxydibenzo[b,f]thiepin in place of the 3-cyano-dibenzo[b,f]thiepin-5,5-dioxide to obtain the title compound.

EXAMPLE 18

8-Hydroxydibenzo[b,f]thiepin-3-carboxaldehyde-5,5-oxide

Repeat the procedure of Example 2 using an equivalent amount of 3-cyano-8-hydroxydibenzo[b,f]thiepin-5,5-dioxide in place of 3-cyano-dibenzo[b,f]thiepin-5,5-dioxide to obtain the title compound.

EXAMPLE 19

8-Methylthiodibenzo[b,f]thiepin-3-carboxaldehyde

Repeat the procedure of Example 3, substituting 3-cyano-8-methylthio-dibenzo[b,f]thiepin in place of 3-cyano-dibenzo[b,f]thiepin to obtain the title product.

EXAMPLE 20

8-Methylsulfinyldibenzo[b,f]thiepin-3-caroxaldehyde

Repeat the procedure of Example 6 using an equivalent amount of 8-methylthiodibenzo[b,f]thiepin-3-carboxaldehyde in place of 10,11-dihydrodibenzo[b,f]thiepin-3-carboxaldehyde to obtain the title product.

EXAMPLE 21

8-Methylthiodibenzo[b,f]thiepin-3-carboxaldehyde-5-oxide

Dissolve 8-methylthiodibenzo[b,f]thiepin-3-carboxaldehyde (5 mmole) in methylene chloride (100 ml); and while cooling the solution in an ice-bath, add a 1M solution of 90% nitric acid in methylene chloride (5 ml). Monitor the reaction mixture by tlc after 30 minutes, and add the nitric acid solution in small increments until starting material has disappeared. Treat the reaction mixture with sodium bicarbonate solution to remove acidic substances. Dry the organic solution, evaporate to dryness, and purify the title product by column chromatography on silica gel using 1:4 ethyl acetate/toluene for elution.

EXAMPLE 22

8-Methylsulfinyldibenzo[b,f]thiepin-3-carboxaldehyde-5-oxide

Repeat the procedure of Example 21 using 3 to 5 equivalents of 1M nitric acid in methylene chrloride in place of slightly more than one equivalent to obtain the title compound.

EXAMPLE 23

8-Methylthiodibenzo[b,f]thiepin-3-carboxaldehyde-5,5-dioxide

React 8-methylthiodibenzo[b,f]thiepin-3-carboxylic acid-5,5-dioxide with excess thionyl chloride under reflux until conversion to the acid chloride is complete. Distill off excess thionyl chloride under vacuum and remove the last traces by adding benzene to the residue and evaporating under vacuum.

Dissolve the crude 8-methylthiodibenzo[b,f]thiepin-3-carboxylic acid chloride-5,5-dioxide in glyme, and with stirring under dry nitrogen, add a filtered solution of 1.1 equivalents of lithium tri-tertiary butoxy-aluminum hydride in glyme dropwise with cooling (ice-bath). Stir the mixture for 1 hour after the addition is complete and pour into ice-cold dilute hydrochloric acid. Isolate the crude title compound by extraction with chloroform and purify the compound by column chromatography on silica gel usin toluene as the solvent.

EXAMPLE 24

8-Methylsulfinyldibenzo[b,f]thiepin-3-carboxaldehyde-5,5-dioxide

Repeat the procedure of Example 6, substituting an equivalent quantity of 8-methylthiodibenzo[b,f]thiepin-3-carboxaldehyde to obtain the title product.

EXAMPLE 25

8-Methylsulfonyldibenzo[b,f]thiepin-3-carboxaldehyde

Repeat the procedure of Example 23, substituting 8-methylsulfonyldibenzo[b,f]thiepin-3-carboxylic acid in place of 8-methylthiodibenzo[b,f]thiepin-3-carboxylic acid-5,5-dioxide to obtain the title product.

EXAMPLE 26

8-Nitrodibenzo[b,f]thiepin-3-carboxaldehyde

Heat a mixture of 8-nitrodibenzo[b,f]thiepin-3-carboxylic acid and excess thionyl chloride under reflux until conversion to the acid chloride is complete. Evaporate excess thionyl chloride under vacuum and remove traces of thionyl chloride from the product by treating the residue with benzene and evaporating again under vacuum.

Stir a mixture of the crude 8-nitrodibenzo[b,f]thiepin-3-carboxylic acid chloride in dry tetrahydrofuran at $-78°$ C. under nitrogen, and add dropwise a filtered solution of 1.1 equivalents of lithium tri-tertiarybutoxy-aluminum hydride in tetrahydrofuran. Stir the mixture for 30 minutes at $-78°$ C. and allow to warm to ambient temperature. Add the mixture to ice-cold dilute hydrochloric acid, and isolate the product by extraction with chloroform. Purify the title compound by chromatography on silica gel using a mixture of ethyl acetate and toluene for elution.

EXAMPLE 27

8-Nitrodibenzo[b,f]thiepin-3-carboxaldehyde-5-oxide and 5,5-dioxide

Repeat the procedure of Example 6, substituting 8-nitrodibenzo[b,f]thiepin-3-carboxaldehyde in place of 10,11-dihydrodibenzo[b,f]thiepin-3-carboxaldehyde to obtain the title 5-oxide compound.

Repeat the above procedure using twice the equivalent amount of m-chloroperbenzoic acid to obtain the corresponding 5,5-dioxide.

EXAMPLE 28

8-Methoxydibenzo[b,f]thiepin-3-carboxaldehyde

Repeat the procedure of Example 4, substituting an equivalent quantity of 3-hydroxymethyl-8-methoxydibenzo[b,f]thiepin for the 3-hydroxymethyldibenzo[b,f]thiepin to obtain the title product.

EXAMPLE 29

8-Methoxydibenzo[b,f]thiepin-3-carboxaldehyde-5-oxide

Repeat the procedure of Example 6, substituting an equivalent quantity of 8-methoxydibenzo[b,f]thiepin-3-carboxaldehyde in place of the 10,11-dihydrodibenzo[b,f]thiepin-3-carboxaldehyde to obtain the title 5-oxide compound.

Repeat the above procedure using twice the equivalent amount of m-chloroperbenzoic acid to obtain the corresponding 5,5-dioxide.

EXAMPLE 30

Dibenzo[b,f]thiepin-3-carboxaldehyde oxime, 5,5-dioxide

Suspend 1.01 g (3.74 mmoles) of dibenzo[b,f]thiepin-3-carboxaldehyde-5,5-dioxide in 10 ml 95% ethanol, and add a solution of 0.32 g of hydroxylamine hydrochloride in 0.4 ml of water, stir vigorously, then add a solution of 0.24 g sodium hydroxide in 0.6 ml water. Stir for 1.5 hour at room temperature, then filter the insoluble solid and wash it with water and ether. Dilute the filtrate with water and extract with ethyl acetate to obtain another crop of product. Combine both crops and chromatograph on silica gel, eluting with a 7:2:1 mixture of $CH_2Cl_2$-hexane-ethyl acetate, to obtain pure product, 782 mg, mp: 206°–207°.

Analysis, calc'd: C:63.14, H:3.89; S:11.24; N:4.91. Found: C:63.00, H:3.90; S:11.11; N:4.79.

EXAMPLE 31

Dibenzo[b,f]thiepin-carboxaldehyde O-acetyloxime, 5,5-dioxide

Stir a mixture of 200 mg (0.7 mmole) of dibenzo[b,f]-thiepin-3-carboxaldehyde oxime 5,5-dioxide (from Example 30) 0.80 ml of pyridine and 173 mg acetic anhydride (1.69 mmole) at room temperature for 1 hour. Add 60 ml of ethyl acetate, and wash the mixture with aqueous 2M citric acid, then with aqueous 10% sodium bicarbonate, then with water. Dry and evaporate the organic fraction. Triturate the residue in 1:1 ether-ethyl acetate and filter to obtain the product, 175 mg, mp: 144°–145°

Analysis calc'd: C:62.37; H:4.00; N;4.28; s:9.79. Found: C:62.34; H:4.18; N:4.23; s:9.54.

EXAMPLE 32

3-(Dimethoxymethtyl)dibenzo[b,f]thiepin-5,5-dioxide

Reflux a mixture of 675 mg dibenzo[b,f]thiepin-3-carboxaldehyde-5,5-dioxide in 20 ml methanol containing 50 mg p-toluenesulfonic acid for 4 hours; allow to cool, add excess solid sodium carbonate and evaporate to dryness. Partition the residue between ethyl acetate and water. Evaporate the organic fraction and crystallize the residue from ether-methylene chloride-hexane to obtain the pure acetal 585 mg, mp; 101°–102°

Analysis calc'd: C:6454; H:5.10; S:10.13. Found: C:64.74; H:5.40; S:10.03.

EXAMPLE 33

3-(1,3 Dioxolan-2-yl)dibenzo[b,f]thiepin-5,5-dioxide

To a mixture of 202 mg dibenzo[b,f]thiepin-3-carboxaldehyde-5,5-dioxide and 300 μl of ethylene glycol in 5 ml of benzene add a crystal of p-toluene-sulfonic acid, then reflux with azeotropic removal of water for 2 hours. After cooling, add excess solid sodium carbonate, then evaporate the benzene and partition the residue between water and ethyl acetate. Evaporate the organic fraction to obtain the pure acetal as a white solid, 218 mg, mp; 128°–129°

Analysis calc'd: C:64.95; H:4.49; S:10.20. Found: C:64.81; H:4:78; S:9.96.

EXAMPLE 34

3-(n-Butyliminomethyl)dibenzo[b,f]thiepin-5,5-dioxide

Reflux a mixture of 200 mg of dibenzo[b,f]thiepin-3-carboxaldehyde-5,5-dioxide (0.74 mmole) and 82 mg of n-butylamine (1.11 mmole) in 0.30 ml of benzene, with azetropic removal of water, for 45 minutes. Evaporate the mixture to remove the benzene and excess butylamine and obtain the title product as an oil.

EXAMPLE 35

3-(Phenyliminomethyl)dibenzo[b,f]thiepin-5,5-dioxide

Heat a mixture of 675 mg (2.5 mmoles) of dibenzo[b,f]thiepin-3-carboxaldehyde-5,5-dioxide and 465 mg of aniline (5 mmoles) in 20 ml of toluene, under reflux, with azetropic removal of water for 21 hours. Cool the mixture and filter the insoluble product. Stir the solid in 10 ml of ether containing a few drops of THF for 10 minutes then filter to obtain the pure product, 704 mg, mp: 184°–185°.

Analysis calc'd: C:73.02; H:4.38; N:4.06; S:9.28. Found: C:73.33; H:4.34; N:4.17; S:9.17.

The compounds of formula I wherein Z is defined as sulfinyl are capable of existing as optical isomers because of the tetrahedral structure of the sulfoxide substituent. Thus, the sulfoxide disclosed in the Examples are racemic mixtures of D and L isomers which may be resolved by known procedures into their enantiomers. Each of the enantiomorphic isomers may exhibit variation in biological potency. Thus, for example, the compounds of Examples 4, 6, 9, 12, 21, 22, and the 5-oxide compounds prepared in 16, 27, and 29, may be resolved by conventional procedures into their D and L enantiomorphs.

The compounds of formula I are useful in the treatment or prophylaxis of mammalian disease conditions where excessive undesirable contractile activity of prostaglandins, such as $PGF_{2\alpha}$, or prostaglandin biosynthetic intermediates contribute. These conditions include asthma, inflammatory states such as arthritis, allergy, diarrhea, hypertension, angina, platelet aggregation, cerebral spasm, premature abortion, and dismenorrhea. In particular, they are of value in reaginic mediated asthma (extrinsic asthma).

The magnitude of a prophylactic or therapeutic dose of compound of formula I will, of course, vary with the nature and the severity of the condition to be treated and with the particular compound of formula I and its route of administration. In general, the dose range lies within the range of 0.2 mg to 100 mg per kg body weight of a mammal.

The pharmaceutical compositions of the present invention comprise a compound of formula I as an active ingredient, and may also contain pharmaceutically acceptable carrier and optionally other therapeutic ingredients. The compositions include compositions suitable for oral, rectal, ophthalmic, pulmonary, nasal, dermal, topical, or parenteral (including subcutaneous, intramuscular, and intravenous) administration, although the most suitable route in any given case will depend on the nature and severity of the condition being treated and on the nature of the active ingredient. They may be conveniently presented in unit dosage form and prepared by any of the methods well known in the art of pharmacy.

For use where a composition for intravenous administration is employed, a suitable dosage range is from 0.2 to 10 mg (preferable 1 to 5 mg) of a compound of formula I per kg of body weight per day, and in the case where an oral composition is employed a suitable dosage range is about, e.g., 1 to 50 mg of a compound of formula I per kg of body weight per day, preferable from 10 to 40 mg/kg.

Pharmaceutical compositions of the present invention suitable for oral administration and by inhalation in the case of asthma therapy may be presented as discrete units such as capsules, cachets, or tablets each containing a predetermined amount of the active ingredient; as a powder or granules; or as a solution or a suspension in an aqueous liquid, a non-aqueous liquid, an oil-in-water emulsion, or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Desirably, each tablet contains from 50 mg to 500 mg of the active ingredient and each cachet or capsule contains from 50 mg to 500 mg of the active ingredient.

Although the instant invention has been described in the foregoing specification in terms of the use of the novel thiepin disclosed herein in the treatment and control of human and warm-blooded animal disease conditions characterized by excessive undesirable contractile activity of prostaglandins and prostaglandin biosynthetic intermediates, and particularly of asthma, it will be recognized by those skilled in the art that, in addition to the involvement of contractile prostaglandins in chronic obstructive lung disease (e.g., asthma), prostaglandins play a role in other allergic conditions as well as in inflammation, diarrhea, hypertension, angina, cerebral spasm, premature abortion, and dysmenorrhea. Also, the thiepins of this invention are potent $TXA_2$ biosynthesis inhibitors, inhibiting platelet aggregation, and can be useful in diseases such as atherosclerosis, varient anginal and myocardial infarction. Applicants consider application of and control of such disease conditions to be obvious equivalents to the invention as disclosed by Applicants and to fall within the scope of the instant invention.

The subject matter which Applicants regard as their invention, and which is sought to be patented herein, is particularly pointed and distinctly claimed as follows.

What is claimed is:

1. A compound of the formula:

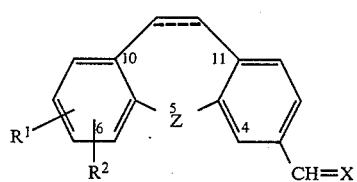

I wherein
X is O, N—$R^3$, wherein $R^3$ is hydrogen, loweralkyl, aryl, hydroxy, loweralkoxy, loweracyloxy, amino or loweralkylamino; or X may have the formula:

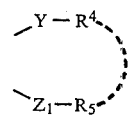

wherein
Y and $Z_1$ are each independently O or S and
$R^4$ and $R^5$ are each independently hydrogen or loweralkyl; and the broken line represents a possible bond between $R^4$ and $R^5$ when $R^4$ and $R^5$ are not hydrogen;
$R^1$ and $R^2$ are each independently hydrogen, halogen including chloro, bromo, fluoro and iodo, amino, $C_1$ to $C_4$ alkanoyl, hydroxyl, $C_1$ to $C_4$ alkoxy, thiol, $C_1$ to $C_4$ alkylthio, $C_1$ to $C_4$ alkylsulfinyl, $C_1$ to $C_4$ alkylsulfonyl, trifluoromethyl, trifluoromethylthio, cyano, nitro, and $C_1$ to $C_4$ alkyl or dialkylamino, benzyl, phenethyl or hydroxyalkyl; and the dotted line indicates either an olefinic bond or saturation at the 10-, 11-position.

2. The compounds of claim 1:
dibenzo[b,f]thiepin-3-carboxaldehyde-5,5-dioxide;
dibenzo[b,f]thiepin-3-carboxaldehyde-5,5-dioxide;
dibenzo[b,f]thiepin-3-carboxaldehyde-5-oxide;
10,11-dihydro-dibenzo[b,f]thiepin-3-carboxaldehyde-5-oxide;
10,11-dihydro-dibenzo[b,f]thiepin-3-carboxaldehyde-5,5-dioxide;
8-fluoro-dibenzo[b,f]thiepin-3-carboxaldehyde-5-oxide;
8-fluoro-dibenzo[b,f]thiepin-3-carboxaldehyde-5,5-dioxide;
8-fluoro-10,11-dihydrodibenzo[b,f]thiepin-3-carboxaldehyde-5-oxide;
8-fluoro-10,11-dihydrodibenzo[b,f]thiepin-3-carboxaldehyde-5,5-dioxide;
8-aminodibenzo[b,f]thiepin-3-carboxaldehyde-5,5-dioxide;
8-chlorodibenzo[b,f]thiepin-3-carboxaldehyde-5-oxide and 5,5-dioxide;
8-hydroxydibenzo[b,f]thiepin-3-carboxaldehyde-5,5-dioxide;
8-methylthiodibenzo[b,f]thiepin-3-carboxaldehyde-5-oxide;
8-methylsulfinyldibenzo[b,f]thiepin-3-carboxaldehyde-5-oxide;
8-methylthiodibenzo[b,f]thiepin-3-carboxaldehyde-5,5-dioxide;
8-methylsulfinyldibenzo[b,f]thiepin-3-carboxaldehyde-5,5-dioxide;
8-nitrodibenzo[b,f]thiepin-3-carboxaldehyde-5-oxide and 5,5-dioxide;
8-methoxydibenzo[b,f]thiepin-3-carboxaldehyde-5-oxide;
dibenzo[b,f]thiepin-3-carboxaldehyde oxime, 5,5-dioxide;
dibenzo[b,f]thiepin-carboxaldehyde O-acetyloxime, 5,5-dioxide;
3-(dimethoxymethyl)dibenzo[b,f]thiepin-5,5-dioxide;
3-(1,3-dioxolan-2-yl)dibenzo[b,f]thiepin-5,5-dioxide;
3-(n-butyliminomethyl)dibenzo[b,f]thiepin-5,5-dioxide;
3-(phenyliminomethyl)dibenzo[b,f]5,5-dioxide.

3. A compound according to claim 1 where Z is sulfinyl and the dotted line indicates an olefinic bond.

4. A compound according to claim 1 where Z is sulfinyl and the dotted line indicates saturation.

5. A compound according to claim 1 where Z is sulfonyl and the dotted line indicates an olefinic bond.

6. A compound according to claim 1 where Z is sulfonyl and the dotted line indicates saturation.

7. A compound according to claim 3, which is dibenzo[b,f]thiepin-3-carboxaldehyde-5-oxide.

8. A compound according to claim 5, which is dibenzo[b,f]thiepin-3-carboxaldehyde-5,5-dioxide.

9. A compound according to claim 3, which is 8-fluoro-dibenzo[b,f]thiepin-3-carboxaldehyde-5-oxide.

10. A compound according to claim 5, which is 8-fluoro-dibenzo[b,f]thiepin-3-carboxaldehyde-5,5-dioxide.

11. A compound according to claim 4, which is 10,11-dihydrodibenzo[b,f]thiepin-3-carboxaldehyde-5-oxide.

12. A compound according to claim 6, which is 10,11-dihydrodibenzo[b,f]thiepin-3-carboxaldehyde-5,5-dioxide.

* * * * *

UNITED STATES PATENT AND TRADEMARK OFFICE
CERTIFICATE OF CORRECTION

PATENT NO. : 4,535,171

DATED : August 13, 1985

INVENTOR(S) : Joshua Rokach

It is certified that error appears in the above—identified patent and that said Letters Patent is hereby corrected as shown below:

In the Claims:

Col. 17, line 65, after "wherein" and before "X is O" insert --Z is sulfinyl, or sulfonyl;--

Col. 18, line 64, Claim 2 change "3-(phenyliminomethyl)dibenzo[b,f]5,5-dioxide." to --3-(phenyliminomethyl)dibenzo[b,f]thiepin-5,5-dioxide.--

Signed and Sealed this

Fifteenth Day of September, 1987

Attest:

DONALD J. QUIGG

Attesting Officer      Commissioner of Patents and Trademarks